(12) United States Patent
Hristov et al.

(10) Patent No.: US 8,480,737 B2
(45) Date of Patent: Jul. 9, 2013

(54) COLUMELLAR STRUT FOR NASAL TIP SUPPORT

(75) Inventors: Krasimira Hristov, Belle Mead, NJ (US); Gavin Chen, Hillsborough, NJ (US); Jianxin Guo, Livingston, NJ (US); James A. Matrunich, Mountainside, NJ (US)

(73) Assignee: Ethicon, Inc., Somerville, NJ (US)

( * ) Notice: Subject to any disclaimer, the term of this patent is extended or adjusted under 35 U.S.C. 154(b) by 68 days.

(21) Appl. No.: 12/891,019

(22) Filed: Sep. 27, 2010

(65) Prior Publication Data

US 2012/0078367 A1 Mar. 29, 2012

(51) Int. Cl.
*A61F 2/18* (2006.01)
(52) U.S. Cl.
USPC .......................................................... 623/10
(58) Field of Classification Search
USPC .......................................................... 623/10
See application file for complete search history.

(56) References Cited

U.S. PATENT DOCUMENTS

| 4,378,802 | A | | 4/1983 | Ersek | |
|---|---|---|---|---|---|
| 4,457,756 | A | * | 7/1984 | Kern et al. | ..................... 604/286 |
| 5,002,583 | A | | 3/1991 | Pitaru | |
| 5,069,660 | A | | 12/1991 | Grantham | |
| 5,112,353 | A | | 5/1992 | Johansson | |
| D366,526 | S | | 1/1996 | Rizzo | |
| 5,620,452 | A | * | 4/1997 | Yoon | ............................. 606/151 |
| 5,674,286 | A | | 10/1997 | D'Alessio | |
| 5,868,746 | A | | 2/1999 | Sarver | |
| 6,322,590 | B1 | | 11/2001 | Sillers | |
| 2007/0293946 | A1 | * | 12/2007 | Gonzales et al. | ............... 623/10 |
| 2008/0077240 | A1 | | 3/2008 | Saidi | |
| 2008/0196729 | A1 | * | 8/2008 | Browning | ...................... 128/834 |
| 2008/0234818 | A1 | * | 9/2008 | Kang et al. | ..................... 623/10 |
| 2009/0069904 | A1 | * | 3/2009 | Picha | .......................... 623/23.72 |
| 2009/0170927 | A1 | * | 7/2009 | Bezwada | ....................... 514/455 |
| 2009/0177272 | A1 | * | 7/2009 | Abbate et al. | ................ 623/1.42 |
| 2009/0270308 | A1 | * | 10/2009 | Libin et al. | ........................ 514/2 |
| 2010/0185282 | A1 | | 7/2010 | Jung | |

FOREIGN PATENT DOCUMENTS

| DE | 102006023058 B3 | 10/2007 |
|---|---|---|
| EP | 1475056 A1 | 11/2004 |
| WO | WO 2008/153263 A1 | 12/2008 |

OTHER PUBLICATIONS

Yong Dock Kim*, Beyoung Yun Park, Won Jae Lee, "Aesthetic reconstruction of the nasal tip using a folded composite graft from the ear", The British Association of Plastic Surgeons (2004) 57,238-244.
Alberto Echeverry, MD; Jenny Carvajal, MD; and Elsy Medina, MD "Alternative Technique for Tip Support in Secondary Rhinoplasty", , Aesthetic Surgery Journal—Nov./Dec. 2006.
Stuart E. James,F.R.C.S.(Plast.) Martin H. Kelly, M.D. "Cartilage Recycling in Rhinoplasty: Polydioxanone Foil as an Absorbable Biomechanical Scaffold", Plastic and Reconstructive Surgery • Jul. 2008, vol. 122, No. 1, pp. 254:260.

(Continued)

*Primary Examiner* — David Isabella
*Assistant Examiner* — Randy Shay
(74) *Attorney, Agent, or Firm* — E. Richard Skula (57) ABSTRACT

Novel bioabsorbable, columellar strut implants are disclosed. The struts are useful in rhinoplasty and nasal reconstruction surgical procedures. The devices have opposed lateral sides connected to a spine member to form a tissue-receiving channel.

32 Claims, 8 Drawing Sheets

OTHER PUBLICATIONS

David B. Lovicea, Matthew D. Mingroneb, and Dean M, "Grafts and Implants in Rhinoplasty and Nasal Reconstruction", Otolaryngologic Clinics of North America, 32(1):113-141 1999.

Thomas Romo III, Edward S. Kwak "Nasal Grafts and Implantg in Revision Rhinoplasty", , Facial Plast Surg Clin N Am 14 (2006) 373-387.

Thomas Romo III, James M. Pearson "Nasal Implants", , Facial Plast Surg Clin N Am 16 (2008) 123-132.

D. Toriumi, "New Concepts in Nasal Tip Contouring", Archives of Facial Plastic Surgery, vol. 8 May/Jun. 2006.

W. Lawson, A. Reino, D. Seidman ,"The Silicone Columellar Strut, Plastic and Reconstructive Surgery", vol. 97(5) Apr. 1996, pp. 938-943.

International Search Report from International Application No. PCT/US11/053242, dated Dec. 6, 2011.

* cited by examiner

COLUMELLAR STRUT FOR NASAL TIP SUPPORT

FIELD OF THE INVENTION

The field of art to which this invention pertains is bioabsorbable implantable medical devices, in particular bioabsorbable medical devices for use in nasal reconstruction surgical procedures.

BACKGROUND OF THE INVENTION

Rhinoplasty is a complex surgical procedure that involves the modification of underlying nasal structures such as bone, cartilage, ligaments and soft fibro-fatty tissue. The procedure may be performed for a variety of reasons that include improving the aesthetic appearance of the patient's nose; for reconstructive purposes following trauma; correcting various abnormalities of the nose that the patient may present; and, for correcting nasal passage functional problems associated with breathing for both inhalation and expiration. Regardless of the reasons for the rhinoplasty, the surgeon strives to restore or maintain functionality, remediate structural issues, and at the same time address aesthetic factors by creating and/or maintaining certain proportions between the various part of the nose and face.

One of the most challenging aspects of rhinoplasty is generally considered to be the surgery of the lower third of the nose, mainly the nasal tip region. The stability of the nasal tip is important not only for the aesthetic look and appearance of the nose (e.g., tip projection and tip rotation), but also for physiological and anatomical functions such as appropriate inspiration and expiration, facial expression, and shock absorbance in response to facial trauma.

Preserving or creating adequate support of the nasal tip is important for both the immediate post-operative results and, the long-term outcomes over the life of the patient. Due to factors such as scar contracture, thinning of the soft tissue envelope, and weakening of the cartilage structures with aging, some suboptimal results may be observed soon after surgery, and the consequent deficiencies can often become much more obvious, pronounced, apparent, and prevalent with the passage of time, usually about ten to fifteen years later.

It is known that skin thickness is a factor in determining how well the external skin cover will redrape over the underlying structures of the nose post-surgery. Patients with thin skin tend to have stronger cartilaginous structures, but the underlying structures are more visible, and a step-like transition between the bone and the cartilage can be seen. On the other hand, for patients having thick skin, obtaining proper definition and refinement can be a challenge.

One of the major support mechanisms of the nasal tip is the medial crura of the lower lateral cartilage (LLC). The foundation of the nasal tip is determined by the base (anterior nasal spine) and the footplates of the medial crura. Patients who have long and strong medial crura that extend to the nasal spine are more likely to have adequate tip support. In contrast, patients who have short medial crura, and flaring footplates at the mid-columella are more likely to have poor tip support and lose tip projection after surgery.

Various surgical techniques and procedures that provide long-term support to the tip of the nose and stabilization of the nasal base have been used in the past. One of the widely used techniques is the placement of a columellar strut graft. The graft is usually and typically made of autologous septal or rib cartilage, which is sutured between the medial crus of the lower lateral cartilages. The columellar strut graft can extend to the nasal spine or be placed above the nasal spine. Another surgical method or procedure to provide nasal tip projection and support is the "tongue-in-the-groove" technique, wherein the medial crus of the lower lateral cartilages are sutured to the caudal end of the septum. A septal extension graft may also be used to ensure that the nasal tip projection is maintained postoperatively. Although nonabsorbable implants may be used to support the nasal tip, this method of tip support treatment is not preferred by surgeons because of associated complications such as infection, skin necrosis, and implant extrusion, as well as factors such as patient awareness, appearance.

In order to improve existing surgical procedures and patient outcomes, there is a continuing need in this art for low mass columellar struts with geometric characteristics that enhance the associated implantation procedure and provide for superior patient results. In particular, there is a need in this art for novel implants made from bioabsorbable polymers that are useful in nasal reconstruction surgical procedures.

SUMMARY OF THE INVENTION

Accordingly, a novel, bioabsorbable, implantable columellar strut device is disclosed. The strut has a pair of opposed lateral wall members. The wall members have free outer lateral edges, inner ends, outer surfaces and inner surfaces, and opposed side ends. A spine member having a preferably curved cross-section connects the lateral members along their inner ends such that the lateral wall members are preferably at least partially angulated with respect to each other. The wall members are moveable with respect to each other from a first resting position to a second position. The spine member has an inner surface, an outer surface and opposed ends. The strut device has a channel formed between the inner surfaces of the wall members and the inner surface of the spine member. The device has a longitudinal opening between the free outer edges in communication with the channel, and opposed side end openings in communication with the channel. There are a plurality of openings extending through the lateral wall members in communication with the channel. The strut device is made from a bioabsorbable polymer. The channel may be used to receive cartilage. The opening between the free outer edges is larger when the walls are moved to the second position, and the side openings are also larger. When the wall members are in the second position, they may exert a force against tissue contained in the channel.

Another aspect of the present invention is a method of performing a surgical procedure using the above-described strut device, for example a rhinoplasty.

These and other aspects and advantages of the present invention will be more apparent from the following description and accompanying drawings.

DETAILED DESCRIPTION OF THE INVENTION

The novel columellar strut devices of the present invention are made from conventional biocompatible and bioabsorbable materials. The bioabsorbable polymers useful to manufacture the strut devices of the present invention have several desirable properties, including good initial strength and breaking strength retention (BSR) and good bioabsorption, for example after implantation for a period of 6-20 weeks, and essentially complete bioabsorption in about 6-12 months. The devices of the present invention may have a BSR of about 25% to about 75% at 8 weeks, and, the devices may have an in vivo absorption time of about 150 days to about 360 days. In addition, the devices may have a BSR of at least 40% at four weeks after implantation, and, an in vivo absorption time of about 30 days to about 300 days. However other strength and absorption profiles may be designed for a particular application. Particularly suitable polymers may include conventional bioabsorbable polymers such as polydioxanone, polyglycolide lactide-rich copolymers (e.g. 70%-90% lactide), or blends thereof, etc. Suitable absorbable polymers may be synthetic or natural polymers. Suitable biocompatible, bioabsorbable polymers include aliphatic polyesters, poly (amino acids), copoly (ether-esters), polyalkylenes oxalates, polyamides, tyrosine derived polycarbonates, poly (iminocarbonates), polyorthoesters, polyoxaesters, polyamidoesters, polyoxaesters containing amine groups, poly (anhydrides), polyphosphazenes, and combinations thereof. For the purpose of this invention aliphatic polyesters include, but are not limited to, homopolymers and copolymers of lactide (which includes lactic acid, D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, and polymer blends thereof. Natural polymers include collagen, elastin, hyaluronic acid, laminin, and gelatin, keratin, chondroitin sulfate and decellularized tissue. The strut devices of the present invention will preferably be made from the following bioabsorbable polymers: poly(p-dioxanone), co-polymers of poly(lactide-co-glycolide), and the blends thereof.

The term BSR or Breaking Strength retention as used herein is defined to have its conventional meaning, i.e., the breaking strength remaining in the device after a certain period of incubation in vivo or in vitro under a given set of conditions. The term bioabsorbable polymer as used herein is similarly defined to have its conventional meaning, i.e., polymer molecules that can degrade as a result of hydrolysis or interaction with the body fluid, and eventually absorbed and/or excreted completely by the body after a certain period of time.

Figure 1:
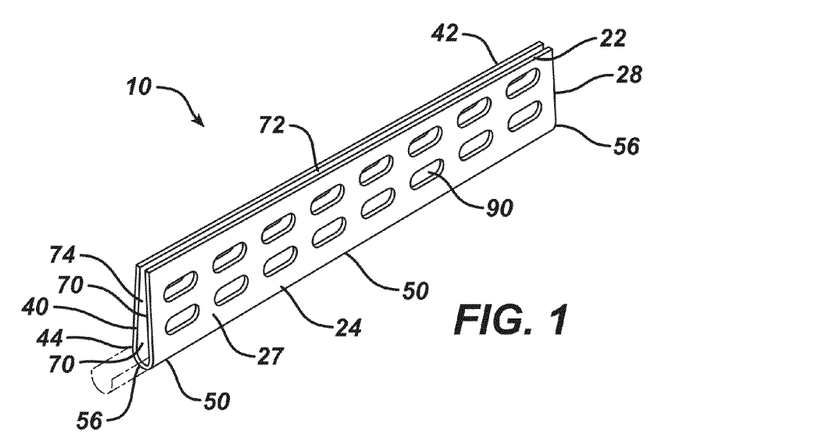
FIG. 1 is a perspective view of an embodiment of a columellar strut device of the present invention; illustrated in phantom lines is an optional extension of the spine member.

Referring to FIGS. 1-4, a columellar strut device 10 of the present invention is illustrated. The strut device 10 is seen to have opposed lateral wall members 20 and 40. Wall members 20 and 40 are seen to have a trapezoidal shape but may have other geometric configurations including rectangular, oval, etc., and may have opposed ends that are straight or optionally rounded or curved. The wall members 20 and 40 are seen to have free outer edges 22 and 42, respectively, separated by opening 72. Wall member 20 has opposed ends 28, and wall member 40 has opposed ends 48. Wall member 20 has inner surface 25 and outer surface 27, and wall member 40 is seen to have inner surface 45 and outer surface 47. The wall members 20 and 40 are also seen to have bottom ends 24 and 44, respectively, connected by spine member 50. Spine member 50 is seen to be an elongated member having a curved cross-section, and having inner surface 52, outer surface 54, and opposed ends 56. Bottom ends 24 and 44 of wall members 20 and 40 are connected preferably along their entire lengths to spine member 50 such that the wall members 20 and 40 are angulated with respect to each other, although the wall members may be attached in sections along the length of the spine member 50. The spine member 50 acts in part as a base member so that the members 20 and 40 may partially deform and rotate toward or away from each other to decrease or increase the size of opening 72. In other words, the wall members 20 and 40 have a first at rest position, and one or both members may be moved to a second position. Although not illustrated, one or both of the wall members 20 and 40 may have a length that is greater than the length of the spine member 50. Conversely, the length of the spine member 50 may be greater, as seen in FIG. 1. Also not illustrated is an embodiment of the present invention wherein the wall members 40 and 50 consist of segments separated by spaces, such that each segment is connected to the spine member 50. An embodiment of the device of the present invention (not illustrated) may have a segmented spine member connecting the walls 40 and 50, wherein the spine member segments are separated by spaces.

The strut device 10 is seen to have channel 70 formed between the inner surfaces 25 and 45 and inner surface 52, extending along the length of the device 10. The device 10 has a longitudinal opening 72 formed between the outer edges 22 and 42, as well as opposed end openings 74. Opening 72 and end openings 74 are in communication with channel 70 in order to provide entry ways for tissue that may be contained partially or completely within channel 70 when device 10 is emplaced in a patient's nose during a surgical procedure, such as a rhinoplasty.

The degree of angulation of wall members 20 and 40 with respect to each other (see FIG. 3) will be sufficient to effectively allow for secure holding of tissue or cartilage, for example tissue or cartilage pieces during preparation of a compound graft where pieces of cartilage are placed in the channel 70. Preferably, the wall members will be angulated inwardly as seen in FIGS. 1-4 when in the first at rest position. The angulation may range from about 3° to about 30°, or optionally about 5° to about 45°. The wall members 40 and 50 may also be angulated outwardly with respect to each other when in the resting position. With respect to an outward angulation, the angulation of the wall members may range from about 3° to about 30°, or optionally about 5° to about 45°. Although not necessarily preferred, the wall members 30 and 40 may be parallel when in the first resting position. When deformed and moved apart with respect to each, from a first resting position to a second position, the opening 72 will increase in size, along with end openings 74, and the wall members 20 and 40 will exert a biasing force against tissue, including cartilage, contained in channel 70. The wall members 20 and 40 are additionally seen to contain a plurality of openings 90. Openings 90 extend completely through the respective wall members and are in communication with channel 70. The openings 90 are seen to have an oblong shape, but may have other shapes or configurations including oval, circular, elliptical, square, rectangular, etc. Openings 90 are useful to provide portals for sutures and other tissue fastening devices. The openings 90 also provide pathways for tissue in-growth and for the passage of fluids and nutrients.

A device 500 of the present invention having outwardly angled wall members 520 and 540 is seen in FIGS. 5A-D. The strut device 500 is seen to have opposed lateral wall members 520 and 540. Wall members 520 and 540 are seen to have a generally rectangular shape but may have other geometric configurations including trapezoidal, oval, etc., and may have opposed ends that are straight or optionally rounded or curved. The wall members 520 and 540 are seen to have free outer edges 522 and 542, respectively, separated by opening 572. Wall member 520 has opposed ends 528, and wall member 540 has opposed ends 548. Wall member 520 has inner surface 525 and outer surface 527, and wall 540 is seen to have inner surface 545 and outer surface 547. The wall members 520 and 540 are also seen to have bottom ends 524 and 544, respectively, connected by spine member 550. Spine member 550 is seen to be an elongated member having a curved cross-section, and having inner surface 552, outer surface 554, and opposed ends 556. Bottom ends 524 and 544 of wall members 520 and 540 are connected preferably along their lengths to spine member 550 such that the wall members 520 and 540 are angulated with respect to each other, although the wall members may be attached in sections along the length of the spine member 550. The spine member 550 acts in part as a base member so that the members 520 and 540 may partially deform and rotate toward or away from each other to decrease or increase the size of opening 572. In other words, the wall members 520 and 540 have a first at rest position, and one or both members may be moved to a second position. Although not illustrated, one or both of the wall members 520 and 540 may have a length that is greater than the length of the spine member 550. Conversely, the length of the spine member 550 may be greater. Also not illustrated is an embodiment of the present invention wherein the wall members 540 and 550 consist of segments separated by spaces, such that each segment is connected to the spine member 550. An embodiment of the device of the present invention (not illustrated) may have a segmented spine member connecting the wall members 540 and 550, wherein the spine member segments are separated by spaces.

The strut device 500 is seen to have channel 570 formed between the inner surfaces 525 and 545 and inner surface 552, extending along the length of the device 500. The device 500 has a longitudinal opening 572 formed between the outer edges 522 and 542, as well as opposed end opening 574. Opening 572 and end openings 574 are in communication with channel 570 in order to provide entry ways for tissue that may be contained partially or completely within channel 570 when device 10 is emplaced in a patient's nose during a surgical procedure, such as a rhinoplasty.

The degree of outward angulation of wall members 520 and 540 with respect to each other will be sufficient to effectively to allow for secure holding of tissue or cartilage, for example tissue or cartilage pieces during preparation of a compound graft where pieces of cartilage are placed in the channel 570. The angulation may range outwardly from about 3° to about 30°. When deformed and moved apart with respect to each other, from a first resting position to a second position, the opening 572 will increase in size, along with end openings 574, and the wall members 520 and 540 will exert a biasing force against tissue, including cartilage, contained in channel 570. The wall members 520 and 540 are additionally seen to contain a plurality of openings 590. Openings 590 extend completely through the respective wall members and are in communication with channel 570. The openings 590 are seen to have an oblong shape, but may have other shapes or configurations including oval, circular, elliptical, square, rectangular, etc. Openings 590 are useful to provide portals for sutures and other tissue fastening devices. The openings 590 also provide pathways for tissue in-growth and for the passage of fluids and nutrients. The wall members 520 and 540 if desired may be moved toward each other in the second position when implanted and exercise a biasing force on tissue in and/or about the device 500.

Another embodiment of the strut device of the present invention is illustrated in FIGS. 6A-D. The strut device 100 is seen to have opposed wall members 120 and 140 connected by spine member 150. Spine member 150 preferably has a curved cross-section. The wall members 120 and 140 have free outer edges 122 and 142, respectively, separated by longitudinal opening 172, and bottom ends 124 and 144, respectively. Device 100 is seen to have opposed end openings 174. Wall member 120 is seen to have opposed lateral ends 128, and wall member 140 is seen to have opposed lateral ends 148. Wall members 120 and 140 are seen to have outer surfaces 127 and 147, respectively, as well as inner surfaces 125 and 145, respectively. The bottom ends 122 and 142 are seen to be connected to spine member 150, preferably along their entire length. Spine member 150 is seen to be an elongated member having a curved cross-section, and having inner surface 152, outer surface 154, and opposed ends 156. The spine member 150 acts to support device 100 and also provides for a base connection so that the wall members 120 and 140 may move with respect to each other from a first at rest position to a second position. The wall members 120 and 140 are seen to angulated with respect to each other, and may be angulated inwardly or outwardly. The device 100 contains a channel 170 formed between inners surfaces 125, 145 and 152 for receiving tissue. The channel is in communication with longitudinal opening 172 and opposed end openings 174. Opening 172 increases or gets larger when the wall members 120 and 140 are moved from a first at rest position to a second position. The spine member 150 is also seen to have outwardly extending flange members 160. Flange members 160 function to increase the stiffness and strength of the implant for stronger support or resistance to bulking or bending deformation. Flange members 160 may be curved as seen, or may be flat. The flange members 160 are seen to have optional flared extensions 165 on end 162. The function of the extensions 165 is to stabilize the implant on the nasal spine.

It is advantageous to keep the wall thicknesses of columellar strut devices of the present invention relatively thin while effectively maintaining the functional and structural characteristics of the strut device, for example in the range of about 0.1 mm-0.6 mm. The advantages of thinner walls include relative ease of cutting or shaping the strut device to different shapes or sizes. And, relatively thinner walls additionally provide for a lower mass of foreign materials in a given implant area, which will have benefits including to help decrease the likelihood of device extrusion, sudden loss of integrity or support, or body/tissue reaction due to degradation products. The thinner walls will result in an implant that is sufficiently strong but that does not increase the natural anatomical width of the columellar region.

As previously mentioned, the thickness of the columellar strut walls is sufficient to effectively support the nasal tip and to facilitate the re-attachment of the medial crus of the lower lateral cartilages. Typically, the wall thickness is between about 0.1 and about 0.6 mm, although the wall thickness may be thicker or thinner depending upon such factors as design, polymer selection, etc. The overall dimensions of the strut will be sufficient to effectively support the tip of the nose in wide range of anatomically different patients; for example, the dimensions may be from about 30 mm to about 50 mm in length and about 4 mm to about 8 mm in width. The initial dimensions are typically sized larger than the actual size implanted in the patient so that the device may be customized or fitted by the surgeon to the patient by cutting or trimming the device intraoperatively prior to implantation. Larger starting dimensions allow the surgeon to more easily manipulate the implant during preparation. The spacing between the outer walls is sufficient to effectively contain tissue, for example, between about 1 mm to about 3 mm thickness.

Figure 2:
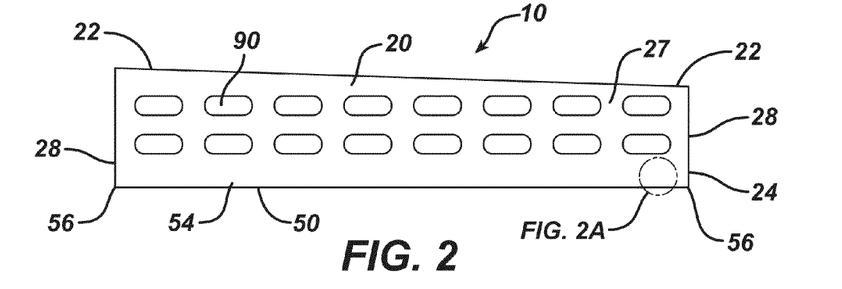
FIG. 2 is a side view of the strut device of FIG. 1.
Figure 2A:
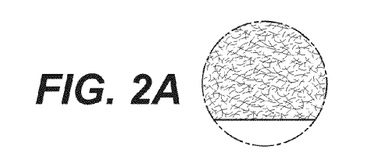
FIG. 2A is a partial magnified view of the strut device of FIG. 1 showing an optional fiber coating.
Figure 3:
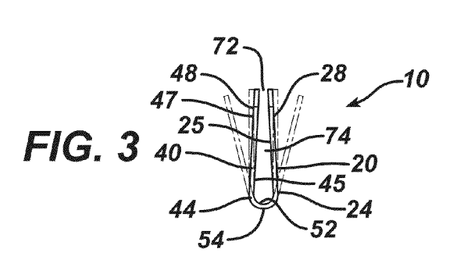
FIG. 3 is and end view of the strut device of FIG. 1.
Figure 4:
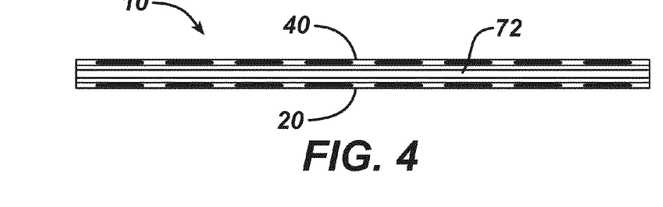
FIG. 4 is a top view of the strut device of FIG. 1.
Figure 5A:
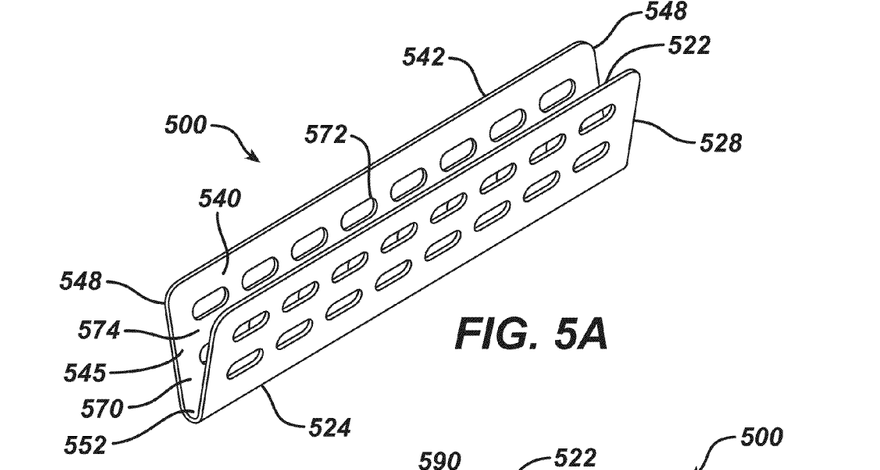
FIGS. 5A-D are perspective, side, end and top views of an embodiment of the strut of FIG. 1 wherein the side members are angulated outwardly.
Figure 5B:
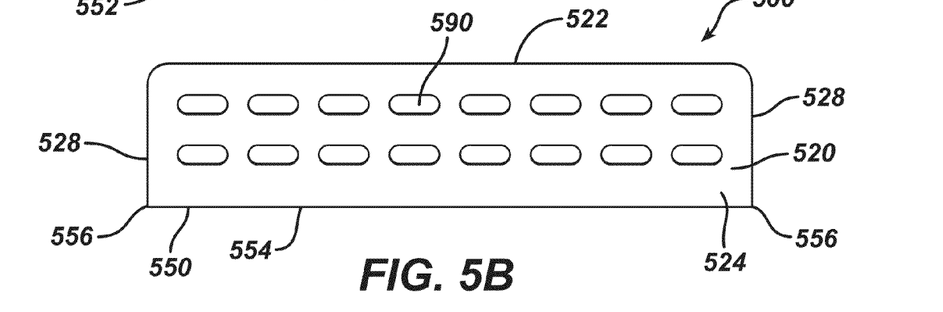
Figure 5C:
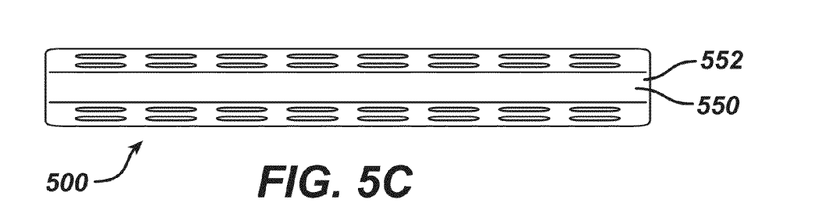
Figure 5D:
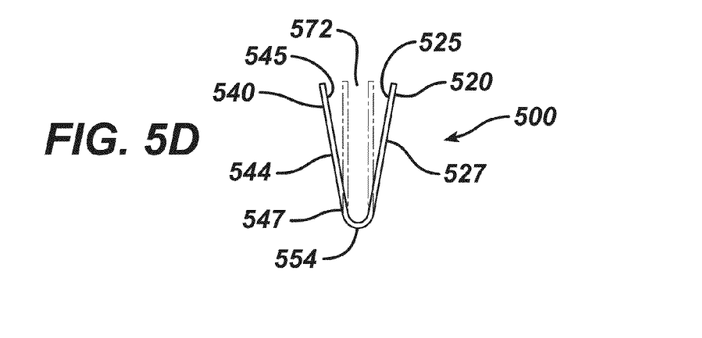
Figure 6A:
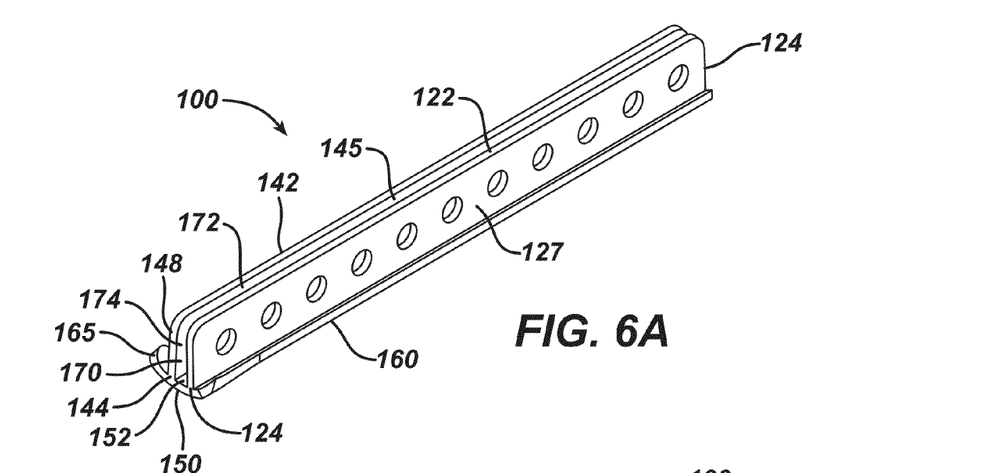
FIG. 6A is a perspective view of an alternative embodiment of the columellar strut device of the present invention wherein the spine member has outwardly extending flanges.
Figure 6B:
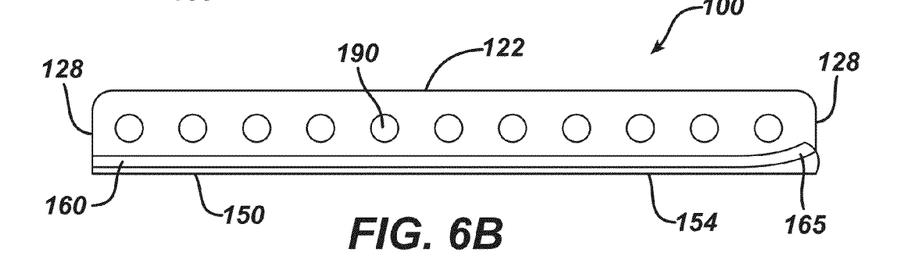
FIG. 6B is a side view of the strut device of FIG. 6A.
Figure 6C:
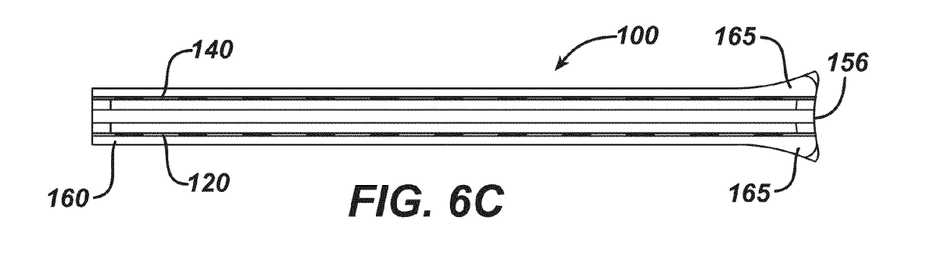
FIG. 6C is a top view of the strut device of FIG. 6A.
Figure 6D:
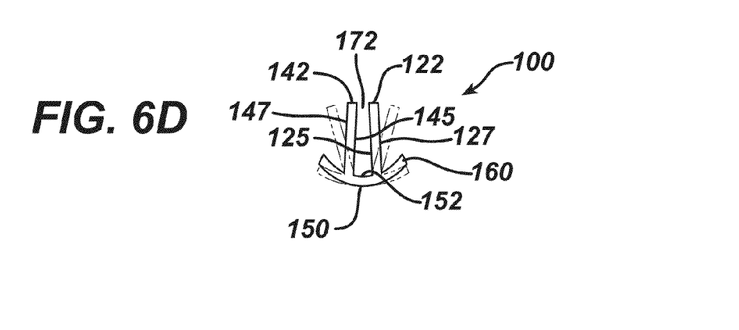
FIG. 6D is an end view of the strut device of FIG. 6A.

The devices of the present invention can be made using conventional manufacturing processes including compression forming, injection molding, thermoforming, profile extrusion, and the like. The devices of the present invention may be optionally coated with various conventional materials including absorbable polymers, biologics, therapeutic agents, absorbable fibers (including microfibers), combinations thereof and the like using conventionally coating processes. For example, coatings may be deposited on the surface by various conventionally known methods including spraying, dipping, immersion, lamination, electrostatic and the like. A coating such as a thin layer of non-woven absorbable material, for example, melt-blown poly(p-dioxanone) nonwoven, can provide faster tissue ingrowth and more comfort to the patient. The coating materials may comprise therapeutic agents such as pharmacologically and/or biologically active agents, including, but not limited to, antibacterial agents, antimicrobial agents, growth factors, and wound healing agents. Active agents may include conventional therapeutic agents for treatment of pain and/or prevention of infection. Examples of active ingredients may include non-steroid anti-inflammatory drugs (NSIADs) such as diclofenac sodium, indomethacine, ketoprofen etc. Other types of active agents suitable to this invention may include conventional antibacterial agents such as triclosan and antibiotics. A columellar strut device of the present invention having an optional coating containing fibers is seen in FIG. 2 and FIG. 2A.

Additionally, the devices of the present invention may be made from a bioabsorbable semi-rigid foam structure. The foam preferably has open and inter-connected pores, although it may also have closed pores. The absorbable foam may be formed by any conventional method. For example, a gas or gas-forming agent may be added to absorbable polymer during or before being extruded to form a foam sheet. A water-soluble agent such as a salt may also be blended with an absorbable polymer to form a solid sheet first.

Conventional lyophylization processes may also be used to form the columellar strut. Those skilled in the art will appreciate that certain of the previously mentioned bioabsorbable polymers may be more useful to form foam structures than others, depending upon their individual characteristics that make them useful in a foam forming process and the desired mechanical characteristics of the device. Some of the polymers that are useful to form foamed structures include poly(p-dioxanone), co-polymers of poly(lactide-co-glycolide) and the blends thereof.

One or more surfaces of the devices of the present invention may optionally have a specific surface roughness to facilitate fixation by increased friction and to create more favorable conditions for cell migration. The surface treatment can be provided in a variety of conventional manners, for example, during injection molding via the mold surfaces or in a surface blasting process similar to sand-blasting. Optionally, micro pores or perforations of about 50-500 μm may be added throughout the surfaces to promote nutrition passage and tissue ingrowth.

Figure 7:
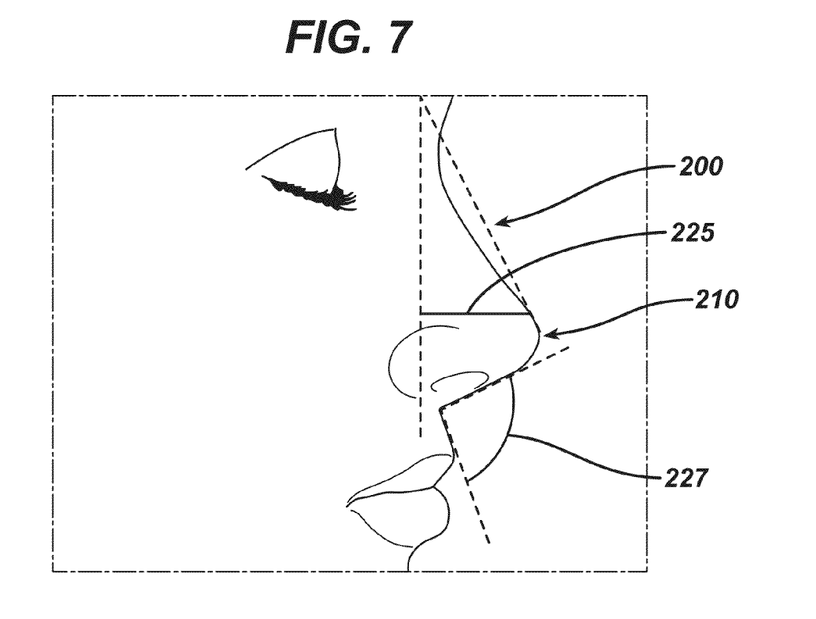
FIG. 7 is an illustration of a nose showing tip projection and tip rotation.
Figure 8:
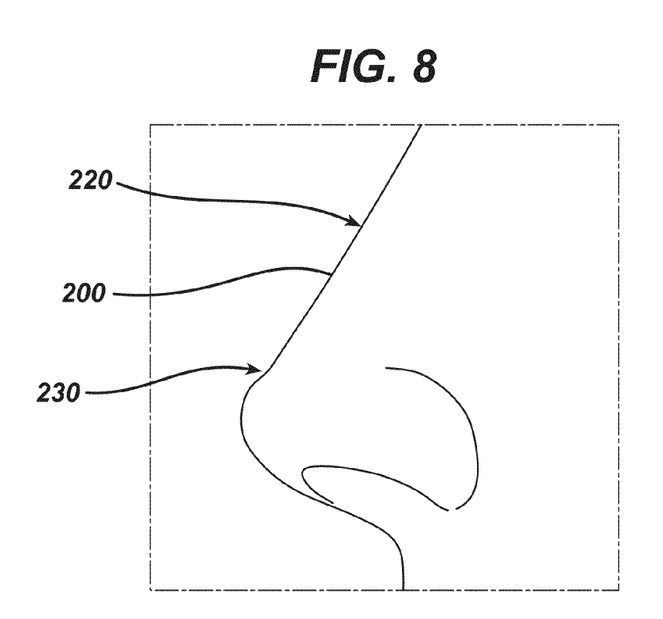
FIG. 8 is an illustration of the nose of FIG. 6 illustrating on the lateral view that the tip projects above the dorsum with a supratip break.

The novel columellar strut devices of the present invention may be used in a variety of nasal reconstruction surgical procedures. It is useful in describing a nasal reconstructive surgical procedure to first review the anatomy of the nose. Referring first to FIGS. 7 and 8, a nose 200 is seen to have a tip region 210, having a projection 225 and a rotation 227. The relationship of the tip 210 to the dorsum 220 is shown. The dorsum of the nose is conventionally defined as the external ridge of the nose, directed forward and upward including the area between the root and the tip of the nose. The supratip break 230 of nose 200 is seen in FIG. 8. The supratip break of a nose is conventionally defined as the point where the straight line of the dorsum changes to a convex curve to define the tip of the nose. The supratip area of a nose is defined as consisting of the distal portions of the upper lateral cartilage 270, the dorsal septum (the dorsal aspect of septum 320), anterior septal angle (the angle of the anterior aspect of the septum 320 relative to the inferior aspect of the septum 320), and the parallel cephalic border of the lateral crura 290 of the lower lateral cartilage 280. Surgery within this area has a profound impact on the tip and can result in polly beak deformity. The tip projection 225 is determined by a line from the nasion to the vermilion border to a perpendicular line to the nasal tip. The nasolabial angle is the angular measure of tip rotation 227 and is defined by the line from the subnasale to the superior vermilion border and the columellar tangent from the subnasale. It ideally is between 90 and 100 degrees in males and 100 and 110 degrees in females.

Figure 9A:
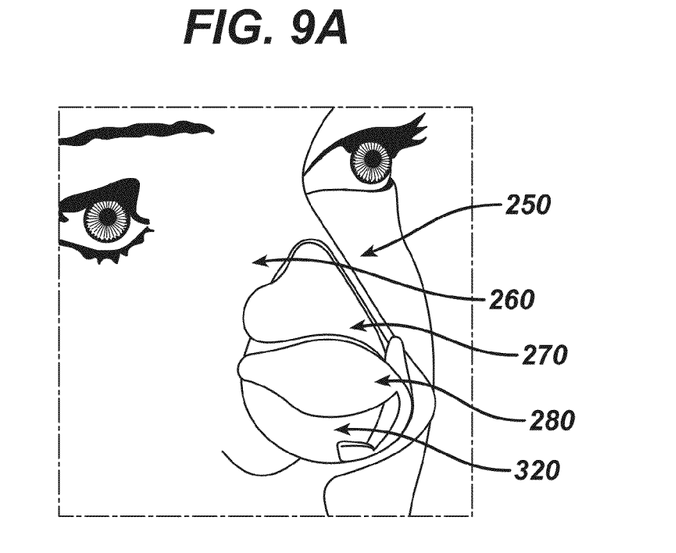
FIGS. 9A and 9B are illustrations showing the major cartilages in the nose.
Figure 9B:
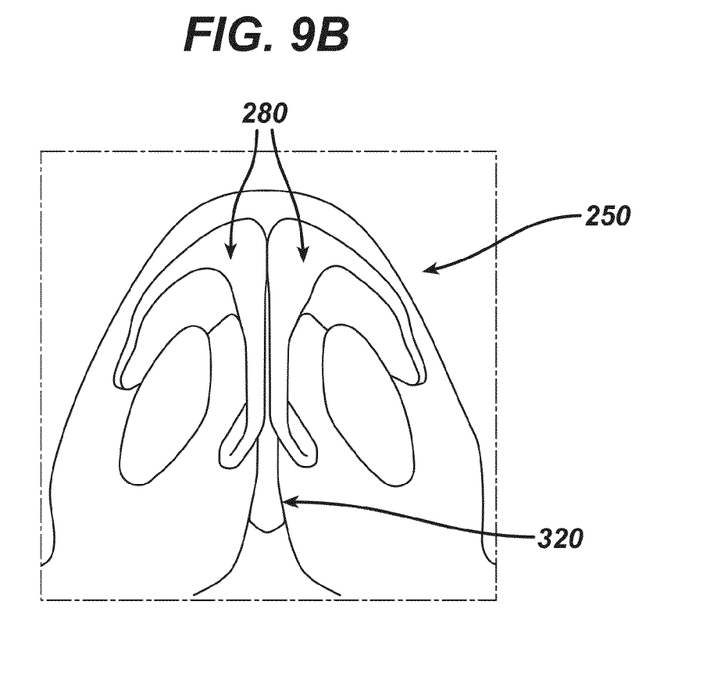
Figure 10A:
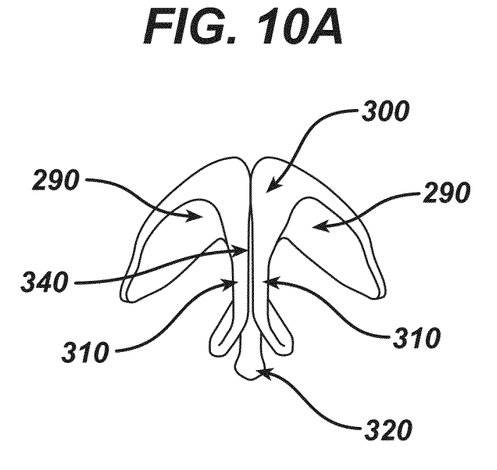
FIGS. 10A and 10B are illustrations showing the crura of the nose and the effect of their positions upon the columellar/lobular angle.
Figure 10B:
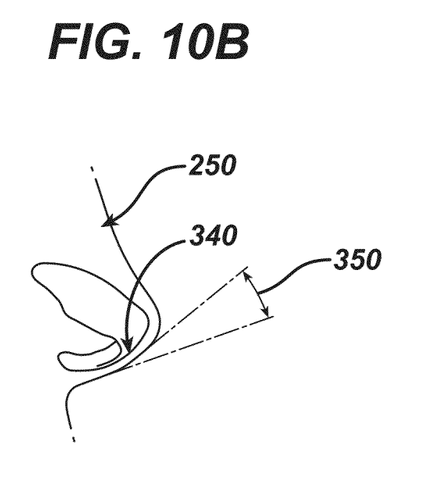

Schematics of the major cartilage structures of the nose are seen in FIGS. 9 and 10. As seen in FIGS. 9A and 9B, the nose 250 is seen to have nasal bones 260, upper lateral cartilages 270, lower lateral cartilages 280, and septum 320. As seen in FIGS. 10A and 10B, the lower lateral cartilages 280 consist of the lateral crura 290, the intermediate crura 300 and the medial crura 310. The right and left medial crura 310 are seen to be separated by septum 320. Also illustrated in FIGS. 10A and 10B is the columellar break point 340 and the columellar/lobular angle 350. The columellar break point 340 is the point of transition of the medial crus 310 and the intermediate crus 300 of the lower lateral cartilages 280. The columellar/lobular angle 350 is the angle formed by the junction of the infra-tip lobule with the columella.

Figure 11A:
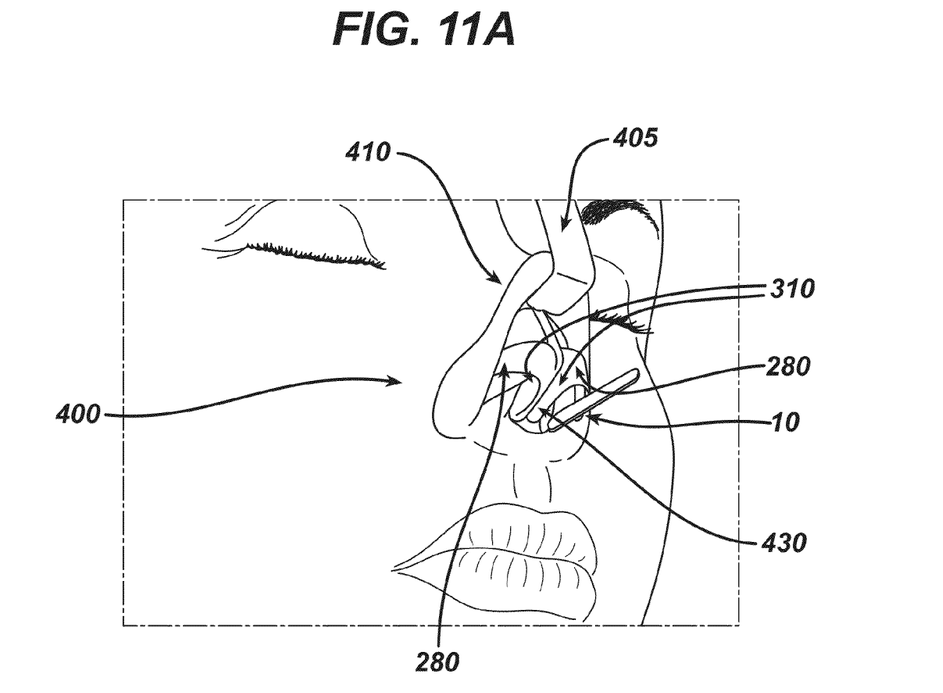
FIGS. 11A-C illustrate a rhinoplasty procedure utilizing the columellar strut of the present invention.
Figure 11B:
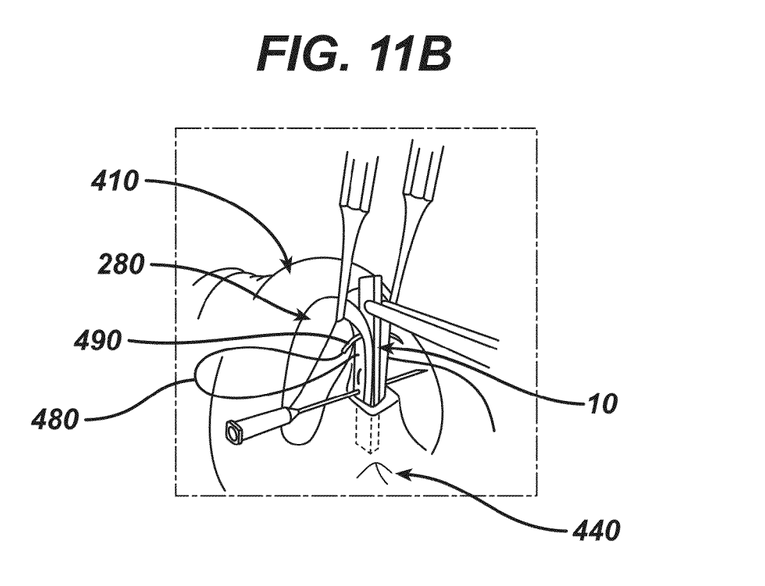
Figure 11C:
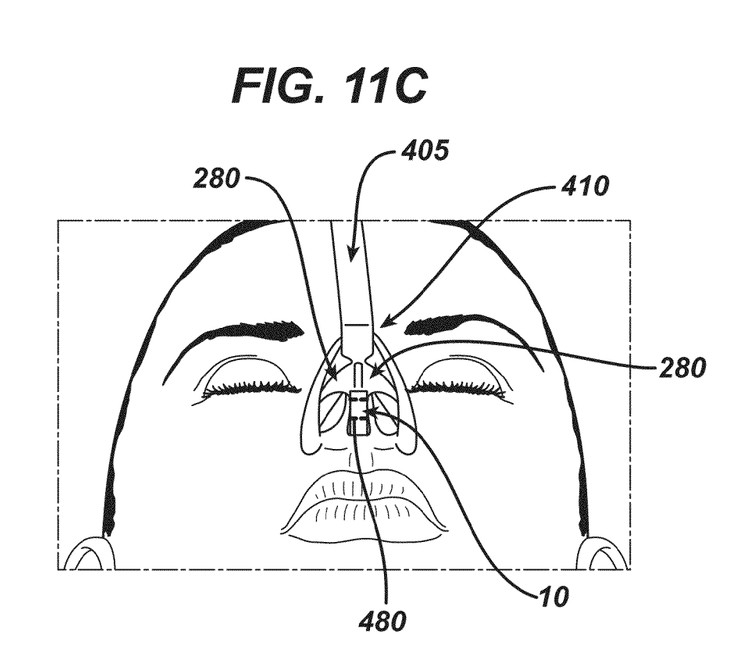

A surgical procedure using a novel columellar strut device of the present invention is illustrated in part in FIGS. 11A-C. Initially, a patient undergoing nasal reconstructive surgery is prepared for surgery in a conventional manner. As seen in FIG. 11A, a soft tissue envelope 410 of nose 400 is elevated to gain access and visualization of the lower lateral cartilages 280. The soft tissue element 410 consists of layers of soft tissue, muscle, and skin. A strut device 10 of the present invention is placed in, fixated, and secured to the patient's nose 400 in the following manner as seen in FIGS. 11 A-C.

A typical rhinoplasty procedure may include one or several of the following steps: elevation of mucpericondrial flaps, correction of airflow, elevation of soft tissue from bone or cartilage, obtaining cartilage grafting material, re-shaping the dorsum, altering the nasal vault and placing various cartilage grafts such as: radix, dorsal onlay, shield graft, alar batten, alar rim grafts, spreader grafts and columela strut graft.

Using an open rhinoplasty approach as illustrated, a transcolumellar step incision is made. The soft tissue skin envelop 410 is dissected and elevated with retractor 405. The final step involving grafts or implants is the placement of the columellar strut 10. A pocket 430 between the medial crus 310 of the lower lateral cartilages 280 is developed. The pocket 430 extends from the columellar incision towards the nasal spine 440 and the depth of this pocket 430 will vary between patients. The columellar strut 10 is placed between the medial crus 310 of the lower lateral cartilage 280. The two medial crus 310 of the lower lateral cartilage 280 are approximated to the columellar strut device 10 and held in position with suture 480 deployed using surgical needle 490, or other surgical fastening devices. The preferred method of fixation is a horizontal mattress suture. In some cases the columellar strut 10 will be additionally fixated with suture to the nasal spine 440. When a closed rhinoplasty approach is used, the lower lateral cartilages 280 are delivered outside of the nose. The approach of placing the columellar strut device 10 is the same.

After the device 10 is secured in place to medial crus 310 of the lower lateral cartilages 280 by sutures 480 as seen in FIG. 11C, the procedure is completed by redraping the soft tissue envelop 410 over the nasal skeleton and then closing the columela skin incision using surgical sutures in a conventional manner.

The following example is illustrative of the principles and practice of the present invention although not limited thereto.

Example 1

A U-shaped columellar strut of the present invention was thermally formed from a flat polymeric sheet made from a blend of 20 wt. % polydioxanone polymer and 80 wt. % of a copolymer of 85/15 poly(lactide-co-glycolide). The plate was extruded using a ⅝" extruder and a 6" slit film die. The extruder and the slit die were manufactured by Randcastle Extrusion systems Inc. of Cedar Grove N.J., USA. The film die had a temperature between about 160° C. and 180° C. The plate had a thickness of about 0.25 mm Strips of the film were punched to produce perforations and the outline of the device. The strut had a width of 8 mm and a length of 30 mm. Two rows of suturing holes of about 1.0 mm wide by 2.5 mm long were formed along a first line of about 3 mm away from the centerline of the spine and a second line of 2 mm from the first line. The holes were formed by die cutting. In a subsequent step the pre-cut devices were placed in a forming set of dies at about 70° C.-75° C. and formed in a U-shape configuration. The formed devices were then placed in a fixture to be annealed with an annealing cycle of heating from room temperature to about 60° C., held at this temperature for about 8 hours, then heated to about 70° C. for 4 hrs, then about 80° C. for 8 hours, and finally cooled down to the room temperature for a period of about 11-13 hrs in N2 atmosphere. The U-shaped columellar strut showed significantly higher resistance to deformation upon loading of a force than a flat plate of similar thickness and size. Based on the simulation using Finite Element Analysis (FEA) method, the critical buckling force was observed to be tripled with the U-shape designed when compared to that of a straight shape of the same thickness.

A tensile test is one of the well known mechanical tests commonly used to evaluate a material's mechanical property (strength, modulus, elongation, etc.). The test determines the tensile breaking strength (or peak tensile force) and the tensile load at a given elongation when a sample is elongated to break or to a pre-determined elongation. An Instron mechanical tester with an appropriate load cell may be used.

Breaking strength retention (BSR) may be determined by in vitro degradation studies at pH 7.2 and 37° C., similar to in vivo conditions. The degradation profile may be obtained until the BSR drops to 20% of the initial breaking strength may be determined.

The absorption profile may be determined in vivo via animal studies or in vitro with conditions similar to the in vivo environment. The material may be considered essentially absorbed when about 90% of the weight of the device is lost by in vitro test or when the traces of the device become essentially disappeared in an in vivo study.

The novel columellar strut devices of the present invention have many advantages when used in rhinoplasty surgical procedures. The advantages include minimal or no need to harvest cartilage to construct a columellar strut graft, which results in shorter procedure and reduced donor site morbidity. The use of the device may result in more predictable long-term outcomes with lower risk of complications.

Although this invention has been shown and described with respect to detailed embodiments thereof, it will be understood by those skilled in the art that various changes in form and detail thereof may be made without departing from the spirit and scope of the claimed invention.

We claim:

1. A bioabsorbable columellar strut device, comprising:
a pair of opposed lateral wall members, said wall members having free outer lateral edges, inner ends, outer surfaces and inner surfaces, and opposed side ends, wherein the wall members have a length, a width, and a thickness, said length is measured along the inner ends between said opposed side ends, said width is transverse to the inner ends and is measured from said free outer lateral edge to said inner end, and said thickness is measured between said outer and inner surfaces, and wherein the length is greater than the width and the width is greater than the thickness;
a spine member, having a length, connecting the lateral members along their inner ends along the length of the spine member such that the lateral wall members are at least partially angulated with respect to each other, and such that the wall members are moveable with respect to each other from a first resting position to a second position, the spine member having an inner surface, an outer surface and a pair of opposed ends, wherein the spine member has at least a partially curved cross-section;
a longitudinal opening between the free edges of the lateral wall members, and opposed side openings between the opposed side ends;
a channel formed between the inner surfaces of the wall members and the inner surface of the spine member, wherein the channel is in communication with the longitudinal opening and the opposed side openings; and,
a plurality of openings extending through the lateral wall members in communication with the channel,
wherein the strut device comprises a bioabsorbable polymer, and wherein wall members exert a force into said channel when in the second position.

2. The device of claim 1, wherein the bioabsorbable polymer is selected from the group consisting of poly(p-dioxanone), co-polymers of poly(lactide-co-glycolide) and the blends thereof.

3. The device of claim 2, wherein the bioabsorbable polymer comprises a blend of poly(p-dioxanone) and poly(lactide-co-glycolide) copolymer.

4. The device of claim 1, wherein the angle of the wall members with respect to each other is about 3° to about 30°.

5. The device of claim 1, wherein the polymer has a BSR of about at least 40% at 4 weeks after implantation.

6. The device of claim 1, additionally comprising a pair of flanges extending out from the spine member.

7. The device of claim 1, wherein the polymer has an in vivo absorption time of about 30 days to about 300 days.

8. The device of claim 1, additionally comprising a coating on at least one part of the surfaces.

9. The device of claim 1, wherein the polymer comprises a foam.

10. The device of claim 1, additionally comprising micropores.

11. The device of claim 1, additionally comprising a therapeutic agent.

12. The device of claim 1, additionally comprising microfibers on the surfaces.

13. The device of claim 1, wherein the spine member has a curved cross-section.

14. The device of claim 1, wherein the wall members are parallel.

15. The device of claim 1, wherein the wall members have a thickness of about 0.1 mm to about 0.5 mm.

16. The device of claim 1, wherein the spine member and the wall members each have a length, and the length of the spine member is greater than the length of the wall members.

17. A method of performing a rhinoplasty, comprising the steps of:
   surgically exposing the lower lateral cartilage of a nose of a patient; and,
   implanting a columellar strut device between the medial crus of the lower lateral cartilages of the nose, wherein the strut device comprises:
   a pair of opposed lateral wall members, said wall members having free outer lateral edges, inner ends, outer surfaces and inner surfaces, and opposed side ends, wherein the wall members have a length, a width, and a thickness, said length is measured along the inner ends between said opposed side ends, said width is transverse to the inner ends and is measured from said free outer lateral edge to said inner end, and said thickness is measured between said outer and inner surfaces, and wherein the length is greater than the width and the width is greater than the thickness;
   a spine member, having a length, connecting the lateral members along their inner ends along the length of the spine member such that the lateral wall members are at least partially angulated with respect to each other, and such that the wall members are moveable with respect to each other from a first resting position to a second position, the spine member having an inner surface, an outer surface, and a pair of opposed ends, wherein the spine member has a length and has at least a partially curved cross-section;
   a longitudinal opening between the free edges of the lateral wall members, and opposed side openings between the opposed side ends;
   a channel formed between the inner surfaces of the wall members and the spine member, wherein the channel is in communication with the longitudinal opening and the opposed side openings; and,
   a plurality of openings extending through the lateral wall members in communication with the channel,
   wherein the strut device comprises a bioabsorbable polymer, and wherein the wall members exert a force upon tissue when in the second position.

18. The method of claim 17, wherein the bioabsorbable polymer is selected from the group consisting of poly(p-dioxanone), poly(lactide-co-glycolide) copolymers.

19. The method device of claim 17, wherein the bioabsorbable polymer comprises a blend of poly(p-dioxanone) and poly(lactide-co-glycolide) copolymer.

20. The method of claim 17, wherein the wall members are angulated and the angle of the wall members with respect to each other is about 5 to about 45 degrees.

21. The method of claim 17, wherein the device has a BSR of about 25% to about 75% at 8 weeks.

22. The method of claim 17, additionally comprising a pair of flanges extending out from the spine member.

23. The method of claim 17, wherein the device has an in vivo absorption time of about 150 days to about 360 days.

24. The method of claim 17, additionally comprising a coating on at least one part of the surfaces.

25. The method of claim 17, wherein the polymer comprises a foam.

26. The method of claim 17, wherein the device additionally comprises micropores.

27. The method of claim 17, wherein the device additionally comprises a therapeutic agent.

28. The method of claim 17, wherein the device additionally comprises microfibers on the surfaces.

29. The method of claim 17, wherein the spine member has a curved cross-section.

30. The method of claim 17, wherein the wall members are angulated with respect to each other and the angulation ranges from about 3° to about 30°.

31. The method of claim 17, wherein the wall members have a thickness of about 0.1 mm to about 0.5 mm.

32. The method of claim 17, wherein the spine member and the wall members each have a length, and the length of the spine member is greater than the length of the wall members.

* * * * *